(12) United States Patent
Li et al.

(10) Patent No.: US 6,462,337 B1
(45) Date of Patent: Oct. 8, 2002

(54) MASS SPECTROMETER ELECTROSPRAY IONIZATION

(75) Inventors: Gangqiang Li, Palo Alto; Hongfeng Yin, San Jose, both of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/552,962

(22) Filed: Apr. 20, 2000

(51) Int. Cl.⁷ ................................................. H01J 49/10
(52) U.S. Cl. ..................... 250/288; 250/423 R; 250/287
(58) Field of Search ............................. 250/288, 423 R, 250/287, 288 A (56) References Cited

U.S. PATENT DOCUMENTS

| | | | |
|---|---|---|---|
| 5,306,910 A | 4/1994 | Jarrell et al. ................. | 250/286 |
| 5,436,446 A | 7/1995 | Jarrell et al. ................. | 250/288 |
| 5,689,111 A | 11/1997 | Dresch ........................ | 250/287 |
| 5,898,175 A | * 4/1999 | Hirabayashi et al. ....... | 250/288 |
| 6,140,640 A | * 10/2000 | Wittmer et al. ............. | 250/288 |
| 6,245,227 B1 | * 6/2001 | Moon et al. ................ | 250/288 |

* cited by examiner

Primary Examiner—Kiet T. Nguyen (57) ABSTRACT

A method of providing ions to a mass spectrometer having an interface member with an orifice through which ions are received for analysis. A fluid is provided at a capillary tip of an electrospray ionization source and a potential difference applied between the tip and the interface member so as to direct an ion beam from the tip toward and through the orifice. A field enhancing potential is applied at an auxiliary electrode so as to increase the electric field gradient from the capillary tip at least part way toward the interface member. A focussing potential may be applied to the auxiliary electrode to generate an electric field which decreases beam divergence from at least part way toward the interface member. Both the field enhancing and focusing potential may alternately be applied to the auxiliary electrode.

30 Claims, 11 Drawing Sheets

MASS SPECTROMETER ELECTROSPRAY IONIZATION

FIELD OF THE INVENTION

This invention relates mass spectrometry and an electrospray ionization source for use in a mass spectrometer which can provide desirable potential distributions for ion generation and/or ion collection.

BACKGROUND OF THE INVENTION

Electrospray ionization (ESI) introduced by Yamashita et al. *Phys. Chem.* 88, p4451, (1984), and Fenn et al., *Science* 246, p64, (1989) is an important method for generating ions for mass spectrometric analysis, and the technique and some of its merits have been particularly described by Smith et al, Anal. Chem., 60, p436, (1988), and others. The merits of ESI include its ability to produce ions from a wide variety of samples such as drugs and biopolymers. Also, ESI is an ideal technique for coupling other chemical separation methods, such as high performance liquid chromatograph (HPLC) or capillary electrophoresis (CE) with a mass spectrometer since ESI can transfer the sample from the liquid phase into the gas phase as required for mass spectrometric analysis.

For mass analysis of ions produced by ESI, almost any type of mass spectrometer can be employed, but time-of-flight mass spectrometers (TOFMS) are widely used, as discussed by Cotter, R. J., *Anal. Chem.* 64, No. 21, p1027A–1039A, (1992). TOFMS is capable of detecting transient signals produced by chromatographic methods because of its high speed of data acquisition. The advantage of using TOFMS for ESI includes unlimited mass range and accurate mass determination which is required for analyzing relatively large biomolecules (>1000 dalton).

An ESI source generates ions at atmospheric pressure while a mass spectrometer requires a pressure of generally under $10^{-4}$ Pascal. Therefore, mass analysis requires introducing the ions into a vacuum chamber. This can be achieved by using an interface plate with a small sampling orifice (typically 0.1 to 2 mm in diameter) between a low pressure chamber of the mass spectrometer and the atmospheric pressure region in which the ESI source operates. As a result, sensitivity of mass detection depends both on ionization efficiency (that is, the number of ions produced by the ESI source) and collection efficiency (that is, the number of ions introduced into vacuum).

Figure 1:
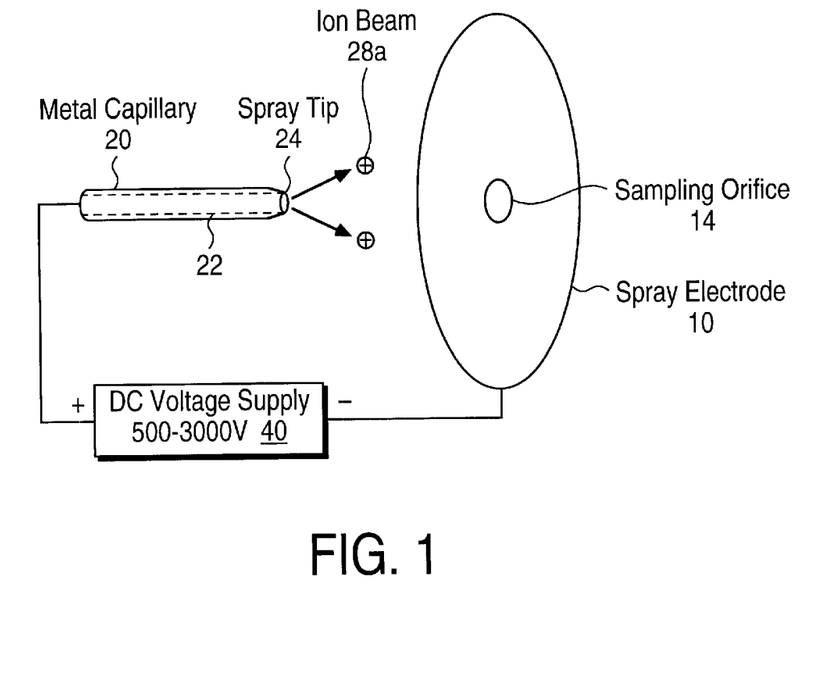
FIG. 1 illustrates a typical conventional ESI source (described above)

A typical conventional ESI source and its operation are illustrated in FIG. 1. Such a source consists of a metal capillary 20 of typically 0.1–0.3 mm in diameter, with a tip 24 held approximately 0.5 to 5 cm (but more usually 1 to 3 cm) away from an electrically grounded circular interface 10 having at its center the sampling orifice 14, such as described by Kabarle et al., *Anal. Chem.* 65, No. 20, p972A–986A, (1993). A potential difference of between 1 to 5 kV (but more typically 2 to 3 kV) is applied to the capillary by power supply 40 to generate a high electrostatic field ($10^6$ to $10^7$ V/m) at the capillary tip 24. A sample liquid carrying the analyte to be analyzed by the mass spectrometer, is delivered to tip 24 through an internal passage 20 from a suitable source (such as from a chromatograph or directly from a sample solution via a liquid flow controller). By applying pressure to the sample in the capillary, the liquid leaves the capillary tip as a small highly electrically charged droplets and further undergoes desolvation and breakdown to form single or multicharged gas phase ions in the form of an ion beam 28a. The ions are then collected by the grounded (or negatively charged) interface plate 10 and led through the orifice 14 into an analyzer of the mass spectrometer. During this operation, the voltage applied to the capillary is held constant. Aspects of construction of ESI sources are described, for example, in U.S. Pat. Nos. 5,838,002; 5,788,166; 5,757,994; RE 35,413; 5,986,258; and others.

The ionization efficiency of ESI is dependent on the electric field formed at the capillary tip. This electric field is furthermore a function of the radius of the capillary tip and the voltage applied to the tip. Small capillary tip radius and high voltage generally produce a high field and hence provide high ionization efficiency. Thus, application of a high voltage between the tip and the interface plate is desirable. However, the present invention realizes that in a conventional ESI source such as of FIG. 1, a high electric field near the tip also generates a very strongly convex potential curvature which results in acceleration of the ions away from the center of the beam. Thus, the ion beam in a conventional ESI source is very divergent. Therefore, even though a large number of ions can be generated in such an ion source, only a small portion (1 to 5%) of these ions can be collected for mass spectrometric analysis because of the small size of the interface orifice and the large ion beam divergence. As a result, the sensitivity of mass analysis is sacrificed.

It would be desirable then if a high field could be provided near the capillary tip of an ESI source, but without causing undue beam divergence. It would also be desirable if a means could be provided in an ESI source to at least reduce beam divergence which might otherwise occur. It would further be desirable if both the foregoing high field and divergence corrections could be provided together in the same ESI source of relatively simple construction.

SUMMARY OF THE INVENTION

The present invention then, provides methods in which ions are provided to a mass spectrometer having an interface member with an orifice through which ions are received for analysis. A fluid is provided at a capillary tip of an electrospray ionization source. First and second electric fields are alternately provided between the tip and the interface member, the first field directing an ion beam from the tip toward and through the orifice, and the second field decreasing beam divergence from at least part way toward the interface member. That is, beam divergence is decreased from what would otherwise result without use of the second field (that is, versus continuous application of the first field). The first and second fields may be provided at a frequency such that the second field is provided when ions emitted from the tip during provision of the first field are intermediate the tip and interface member. In one aspect the mass spectrometer is a time of flight mass spectrometer which moves ions to be analyzed into an analyzing section of the spectrometer at a predetermined pulse rate. In this case the frequency and pulse rate may be synchronized such that a higher ion current is provided to the analyzing section than would be provided if the first field was continuously applied.

In another aspect, an auxiliary electrode may be used to establish or help establish the first and/or second fields. In this aspect, a potential difference between the tip and the interface member is provided so as to direct an ion beam from the tip toward and through the orifice. A field enhancing potential is applied at the auxiliary electrode so as to increase the electric field gradient from the capillary tip at least part way toward the interface member. In another aspect, a focussing potential is applied at an auxiliary electrode so as to decrease beam divergence from at least part way toward the interface member. In another aspect, the same auxiliary electrode provides both the field enhancing and focussing functions by alternately applying the field enhancing and focussing potentials to an auxiliary electrode. Optionally, either the field enhancing or focussing potentials may be provided intermittently at a predetermined frequency. For example, the field enhancing and focussing potentials may be applied alternately at a frequency such that the focussing potential is applied when ions emitted from the tip during application of the field enhancing potential are intermediate the tip and interface member. In the particular case where the mass spectrometer is a time-of-flight mass spectrometer which moves ions to be analyzed into an analyzing section of the spectrometer at a predetermined pulse rate (just as by a suitable pulser), the frequency and pulse rate may be synchronized such that a higher ion current is provided to the analyzing section than would be provided without the use of the auxiliary electrode.

In yet another aspect of the invention, an additional acceleration for all the charged particles is provided due to switching from the first to the second field. This acceleration causes a separation between the ions and those incompletely desolvated charged droplets which normally result in signal noise for a mass spectrometer and therefore are undesirable. As a result of additional acceleration, signal-to-noise ratio of the instrument can be enhanced.

In one particular construction, the auxiliary electrode faces the interface member. The auxiliary electrode may be at least partly behind the capillary tip. For efficiently reducing the beam divergence, the dimension, that is the diameter of the auxiliary electrode, may be chosen to be the same (including about the same) as the distance between the spray tip and the interface member, for example typically 0.5 to 5 cm. In one particular configuration the auxiliary electrode may be positioned around an axis of the capillary and extend forward from a position behind the tip toward the interface member. For example, the auxiliary electrode may be in the form of an open ended cone with the apex centered around the capillary behind the tip.

Field enhancing and focussing potentials can be adjusted as desired for the particular configuration. For example, for field enhancement the potential may be lower than the tip potential when positive ions are being provided and higher than the tip potential when negative ions are being provided. As to the focussing potential, this may be higher than the tip potential when positive ions are being provided and lower than the tip potential when negative ions are being provided. As to the amount of field enhancement, this may be an increase in potential gradient within 0.5 mm of the capillary tip, of at least 10% or at least 20% or 50%. As to the amount by which divergence of the beam is decreased, this may be such that at least 10% more, or at least 20% more (or even at least 50% more) of the generated ions pass through the interface member orifice during one field switching period.

The present invention further provides an electrospray ionization source for use with a mass spectrometer having an interface member with an orifice. The source includes a capillary and optionally the auxiliary electrode, both positioned and operable in any of the manners as described above. In particular, the field enhancing and/or focussing potentials may be applied to the auxiliary electrode so as to provide the effects described above. The invention further provides a mass spectrometer which includes the interface member and electrospray ionization source, both as previously described, as well as an analyzer section which receives ions from the source which have passed through the orifice, and detects them as a function of mass and charge. A power supply may be included to provide any of the previously described potentials to the electrospray ionization source. In the case where the different fields are to be provided at the above described frequency, the mass spectrometer may optionally include a processor which selects the frequency as a function of mass of the ions to be analyzed by the mass spectrometer.

The various aspects of the present invention can provide any one or more of the following and/or other useful benefits. For example, a high field can be provided near the capillary tip without causing undue beam divergence. The invention can also provide a means to at least reduce beam divergence which might otherwise occur. The invention can further improve the signal-to noise ratio by means of charge separation due to field switching. Both the high field and divergence corrections can be provided together in the same ESI source of simple construction.

BRIEF DESCRIPTION OF THE DRAWINGS

Embodiments of the invention will now be described with reference to the drawings, in which.

To facilitate understanding, identical reference numerals have been used, where practical, to designate identical elements that are common to the figures.

DETAILED DESCRIPTION OF EMBODIMENTS OF THE INVENTION

In the present application, unless a contrary intention appears, the following terms refer to the indicated characteristics. Words such as "forward" are used in a relative sense only, generally with forward referring to a direction of ion flow. A "set" may have any number of multiple members (for example, two or more electrodes). Reference to a singular item, includes the possibility that there are plural of the same items present. Potentials are relative, usually with respect to the interface plate unless a contrary indication appears. All patents and other cited references are incorporated into this application by reference.

Figure 2:
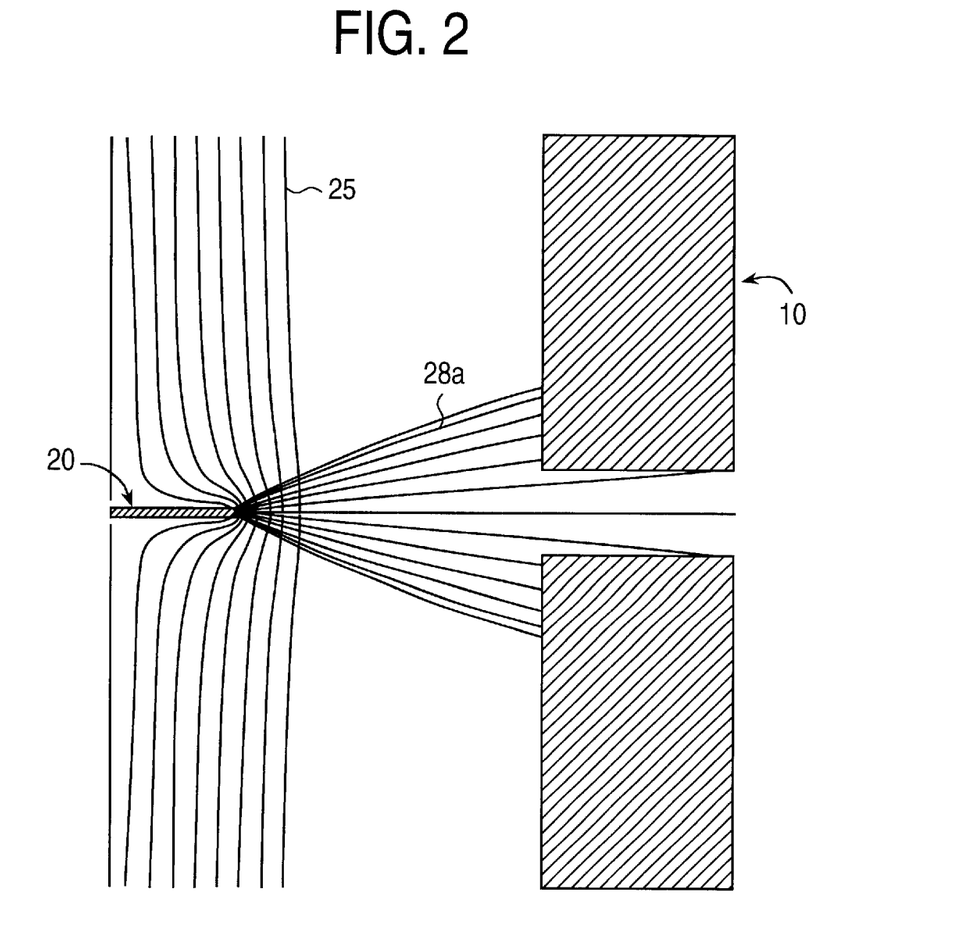
FIG. 2 is a computer simulation for potential distribution and ion trajectories in the ESI source of FIG. 1.

Referring first to FIG. 2, it will be seen from equipotential lines 25 that in a convention ESI source as illustrated in FIG. 1, a convex potential gradient is formed near tip 24 of capillary 20 during operation. This convex potential gradient results in acceleration of the ions away from the center of beam 28a. Thus, the ion beam is divergent in a conventional ESI source, and the degree of divergence of the ion beam increases with increasing electric field. This inherently results in a low collection efficiency of ions from a conventional ESI source since many of the ions in beam 28a will collide with and be neutralized on interface plate 10 before they can enter the remainder of the mass spectrometer.

Figure 3A:
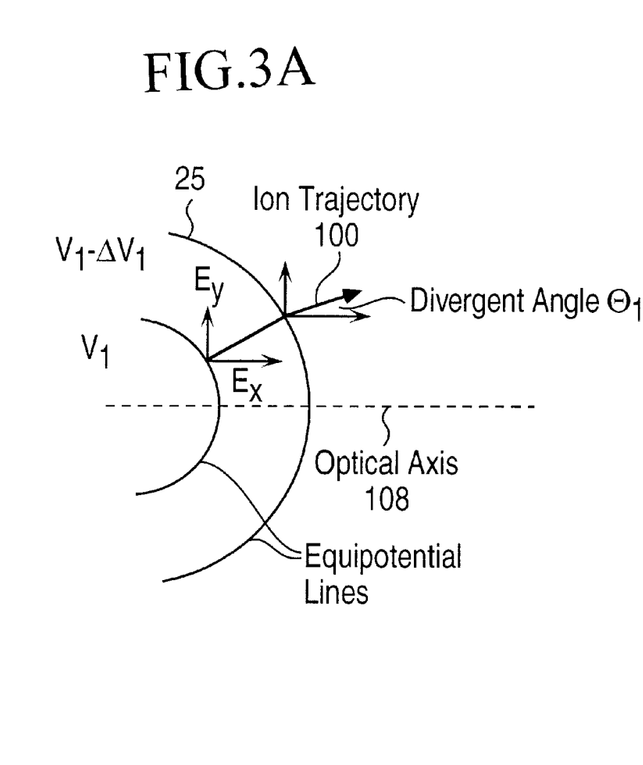
FIGS. 3(a) and 3(b) illustrate in part (A) how a field with positive potential curvature accelerates positively charged ions away from the optical axis causing the ion beam to diverge, and in part (B) how a field with negative potential curvature accelerates positively charged ions towards the optical axis causing the ion beam to be convergent.

The results of the potential gradient near tip 24 can be more clearly understood with reference to FIG. 3A. It will be assume that beam 28a is a positive ion beam, although it will be appreciated that the same concepts apply to negative ions. In particular, near tip 24 equipotential lines 25 $V_1$ and $V_1-\Delta V_1$ have incrementally different potentials $\Delta V_1$. As a result of the size of tip 24 the equipotential lines are convex shaped causing a particular ion trajectory 100 of beam 28a to diverge away from optic axis 108 at an angle $\Theta_1$ determined by the ratio of the electric fields in the y direction ("$E_y$") and x direction ("$E_x$"). The smaller tip 24 and the greater the potential difference between tip 24 and interface member 10, the greater the convexity and hence the greater divergence of beam 28a. While it would be desirable to increase the potential gradient as much as possible near tip 24 in order to improve ionization of the analyte, this will not decrease the divergence angle $\Theta_1$ and could increase it.

Figure 3B:
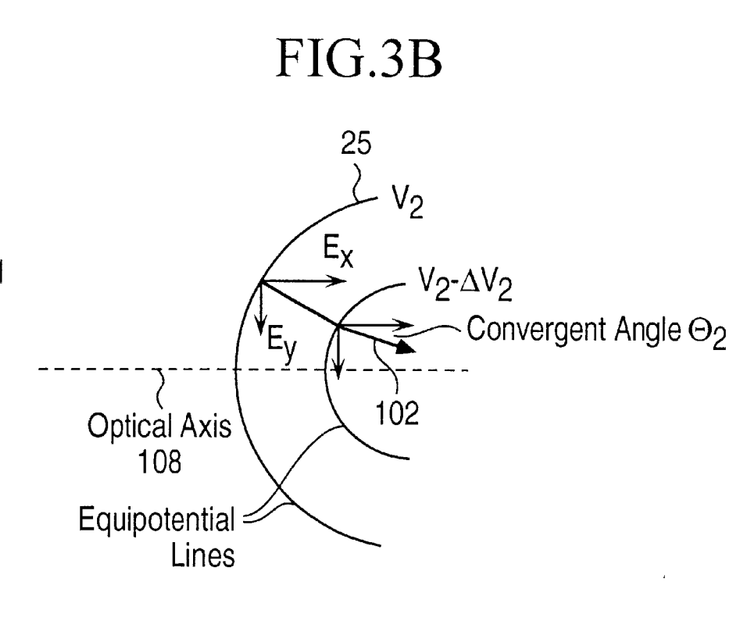

The present invention recognizes that as the ions move toward the interface member 10 they can be focussed along a trajectory 102 which converges toward optic axis 108 at an angle $\Theta_2$ toward sampling orifice 14, by a concave potential gradient as shown in FIG. 3B. While in the conventional ESI source arrangement of FIG. 1 some degree of convergence of beam 28a may take place toward interface member 10 depending upon the relative positions and sizes of tip 24 and interface member 10, it will typically only be very small with little compensation for divergence that has taken place as the ions leave tip 24. Thus, beam 28a is strongly divergent in its overall path between tip 24 and interface member 10. While the electric field between tip 24 and interface member 10 might be altered to increase convergence (that is, increase $\Theta_2$) toward orifice 14, this may have the disadvantage of decreasing the potential gradient near tip 24. However, this disadvantage can be compensated for by alternately providing an ESI source with a first electric field between the tip and the interface member so as to direct an ion beam from the tip toward and through the orifice, and a second electric field which decreases beam divergence from at least part way toward the interface member.

Figure 4:
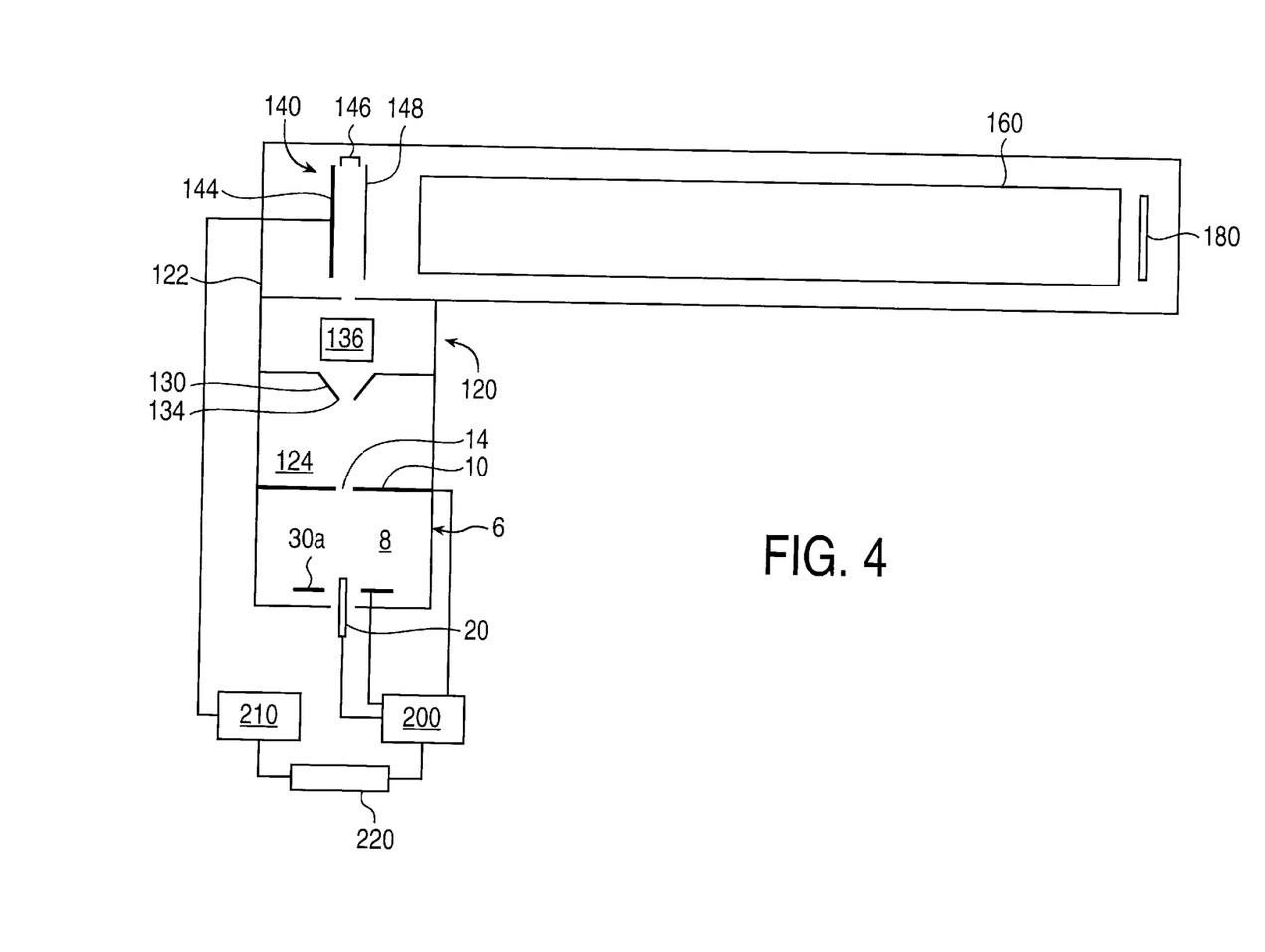
FIG. 4 schematically illustrates a mass spectrometer of the present invention.

A time of flight mass spectrometer ("TOFMS") with an ESI source which can provide the foregoing alternating electric fields, is illustrated schematically in FIG. 4. The illustrated mass spectrometer 120 includes a housing 122, an ESI source 6, and an interface member 10 in the form of a plate having an orifice 14. Downstream (used with reference to the normal direction of ion flow) from ion source 6 is provided a skimmer 130 with skimmer orifice 134, beam formation and guide section 136, a pulser 140, and an analyzer section 160 which includes detector 180. In operation, a chamber 8 of ESI source 6 is maintained at near atmospheric pressure, while chambers 124 and the analyzer section 160 may be maintained at the same or different vacuum levels (with analyzer section being maintained at about less than $10^{-4}$ Pascal). Pulser 140 receives an ion beam from ESI source 6 through orifices 14, 134 and beam formation and guide section 136, onto electrode 146. A pulse is applied between electrode 144 and screen electrode 148 at a pulse rate based on the analyte being analyzed and the characteristics of an analyzer section 160, to extract ion packets from the ion beam otherwise impinging onto electrode 146 of pulser 140, and direct them toward analyzer section 160 which receives the ions and detects them at detector 180 as a function of mass and charge. A power supply 210 typically connected to electrode 144, is used to provide voltages for the ion extraction. One or more pumps (not shown) are provided to maintain required pressures downstream of interface member 10, while a power supply (not shown) is also provided to provide the required potential differences at section 136 and pulser 140. Components of mass spectrometer 120 downstream of interface member 10, and their operation, are well known and are described, for example, in U.S. Pat. No. 5,689,111 and the references cited herein, and are incorporated herein by reference.

Figure 5:
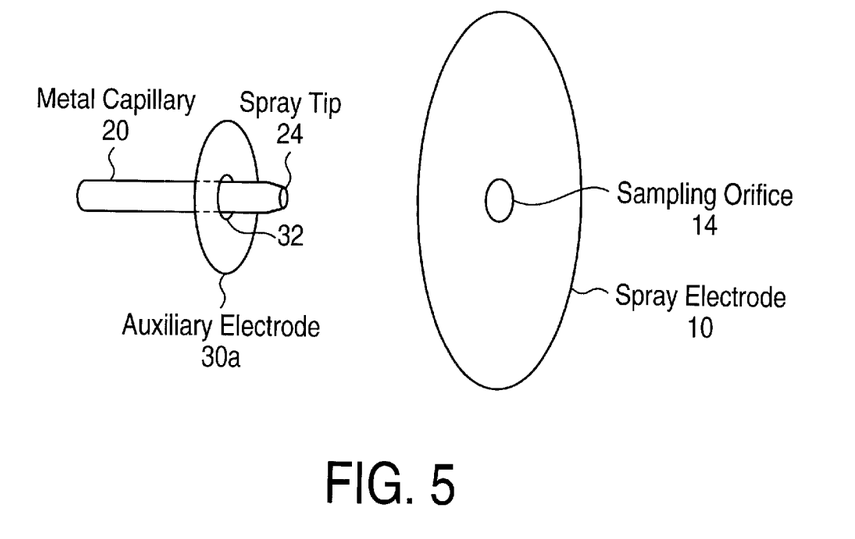
FIG. 5 illustrates an ESI source of the present invention as used in FIG. 4.

ESI source 6 (components of which can be seen more clearly in FIG. 5), includes metal capillary 20 and an auxiliary circular planar electrode 30a having a central opening 32. The components of ESI source 6, other than auxiliary electrode 30a, are constructed, positioned, and operated in the same manner as a conventional ESI source as described above in connection with FIG. 1. As can be seen from FIG. 5 in particular, auxiliary electrode 30a is mounted to extend around an axis of capillary 20 at a position behind tip 24 (with reference to the normal direction of an ion beam emitted from tip 24), and to face interface member 10. Tip 24 is oriented to face orifice 14 so that ions issuing therefrom are directed toward orifice 14. As best seen in FIG. 5, interface member 10 is a circular planar metal plate electrode with orifice 14 in the middle. Capillary 20, auxiliary electrode 30a and interface member 10 are all electrically insulated from one another (and preferably also from the remainder of housing 120) and mounted so that the required potentials can be applied to them to provide the electric fields as described below, by a power supply 200 which is under the control of a processor 220. Processor 220 may include a general purpose digital microprocessor suitably programmed from a computer readable medium carrying necessary program code, to execute all of the steps required of it, or may be any hardware or hardware/software combination which will perform those or equivalent steps. Processor 220 may also control power supply 210 for synchronizing the ion extraction in the analyzer and ESI source operation.

Figure 6:
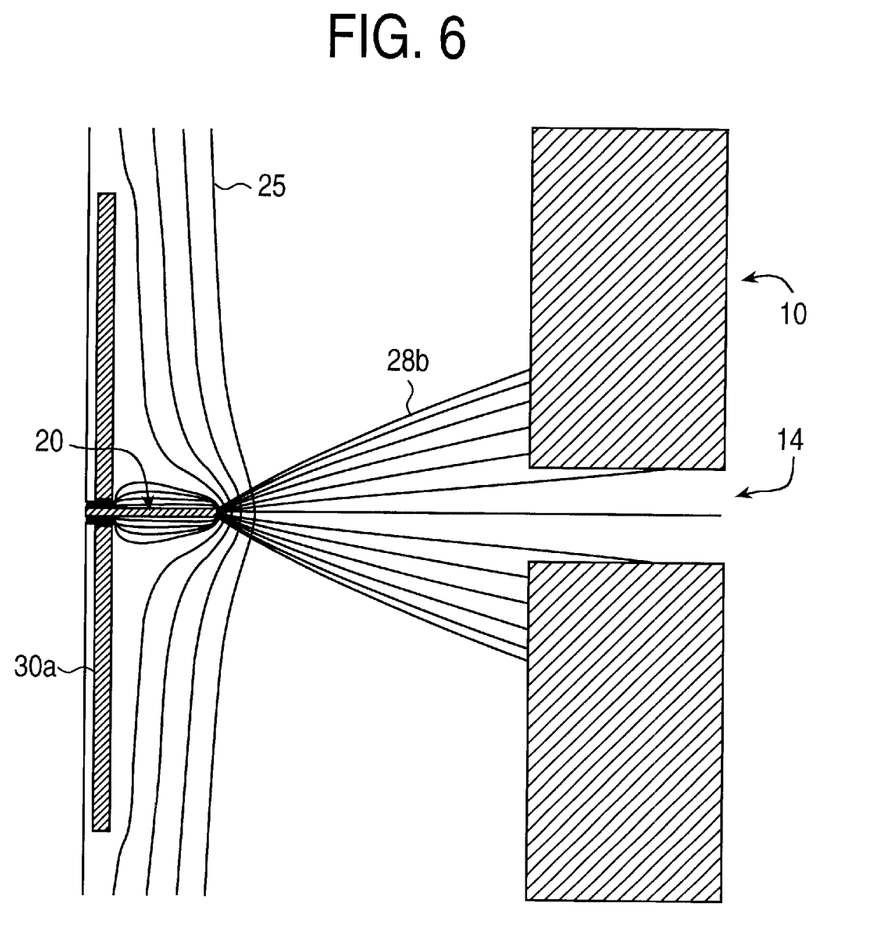
FIG. 6 is a computer simulation of the ESI source of FIG. 4 in operation during an ion generation period of an operational cycle.

In operation of ESI source 6, field enhancing and focussing potentials are alternately applied by power supply 200 to auxiliary electrode 30a. The effect of applying the field enhancing potential is illustrated in FIG. 6, which is the same as FIG. 2 but showing equipotential lines 25 and the path of a resulting ion beam 28b if the field enhancing potential remained constantly ON. A voltage of about 1 to 4 kV is applied to tip 24. This provides a sufficient electric field between tip 24 and interface member 10 so as to direct an ion beam from tip 24 toward and through orifice 14. With positive ion generation, the potential at tip 24 is higher than interface member 10, while the field enhancing potential applied to auxiliary electrode 30a is lower than the potential at tip 24. As can be seen from FIG. 6, application of the field enhancing potential to auxiliary electrode 30a increases the potential gradient near tip 24 while also causing a slightly greater divergence of ion beam 28b. The higher potential gradient near tip 24 enhances analyte ionization efficiency (that is, more ions are produced while the field enhancing potential is ON than would be without the auxiliary electrode 30a). With negative ion generation, tip 24 potential is lower than member 10 potential, while the field enhancing potential is higher than tip 24 potential.

Figure 7:
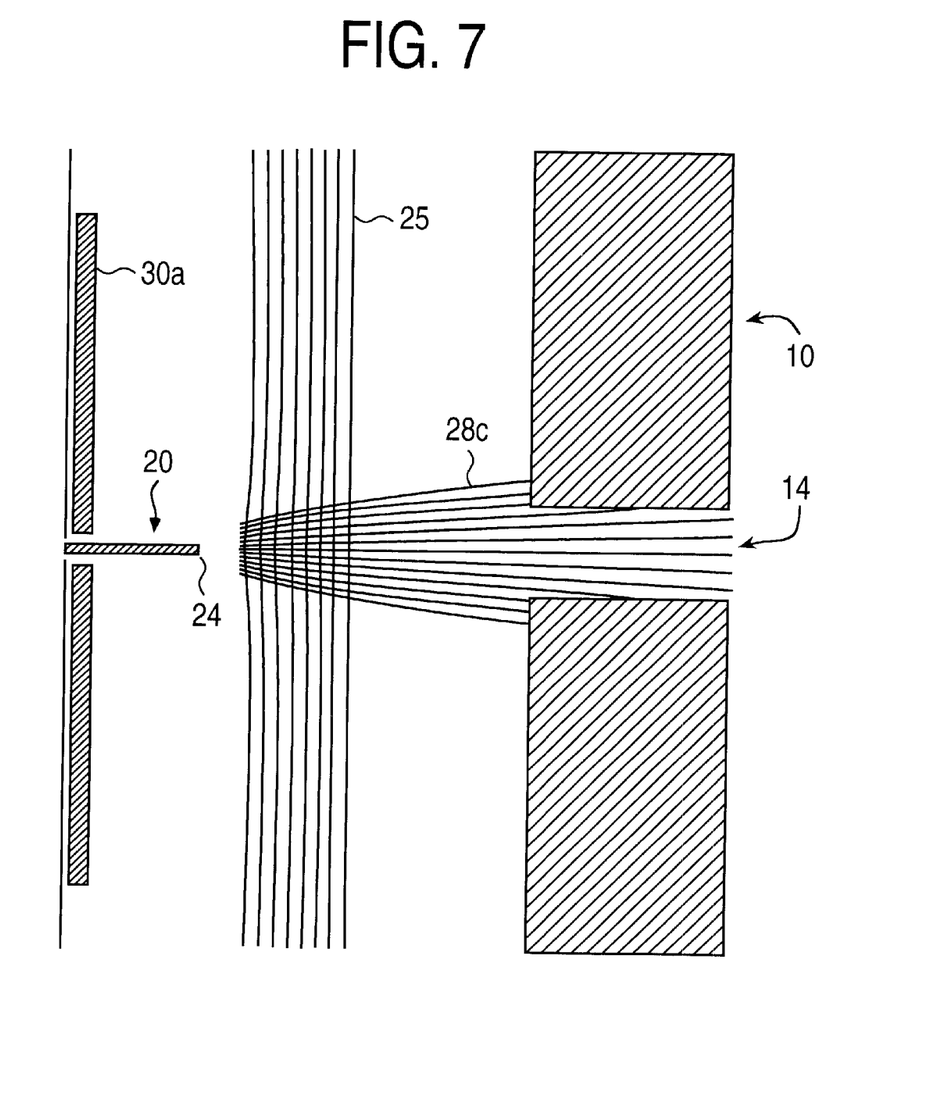
FIG. 7 is a computer simulation of the ESI source of FIG. 4 in operation during the ion collection period, to provide ion focusing.

The effect of applying the focussing potential to auxiliary electrode 30a is illustrated in FIG. 7. FIG. 7 is the same as FIG. 6 with all conditions the same except that the potential applied to auxiliary electrode 30a is now a focussing potential which is higher than the tip 24 potential for positive ion generation, and lower than tip 24 potential for negative ion generation. The result is to cause beam 28c to exhibit a decreased divergence than it otherwise would be in the absence of auxiliary electrode 30a. However, during application of the focussing potential, field gradient at tip 24 will be reduced and hence ion formation there decreased. The net effect will be an ion beam at orifice 10 of varying ion density corresponding to the frequency at which the potential at auxiliary electrode 30a is switched. At least each ion pulse (region of highest ion density) though, will have an ion density which is greater than would be obtained under the same conditions but absent auxiliary electrode 30a.

Power supply 200 may alternately apply field enhancing and focussing potentials at a frequency such that the focussing potential is applied when ions emitted from tip 24 during application of the field enhancing potential are intermediate tip 24 and interface member 10 (specifically, orifice 14). For example, the potential could be switched when such ions are about mid-way between tip 24 and member 10. Such a switching method has the advantage of providing increased ionization efficiency at tip 24 during application of the field enhancing potential, while also decreasing divergence of the initially divergent ion beam during application of the focussing potential, than would otherwise be obtained in the absence of auxiliary electrode 30a. This frequency may be synchronized with the pulse rate of ion packet extraction at pulser 140. That is, the frequency is adjusted such that pulses of maximum ion density will be between electrodes 144, 148 just as pulser 140 is operated to extract an ion packet for provision to mass analyzer 160. The net result will be that a higher ion current is delivered to analyzer section 160 than would be provided without the use of auxiliary electrode 30a. Furthermore, based on the foregoing computer simulations, total ion current through sampling orifice 14 may, for example, be enhanced from 2 to up to 5 to 10 times. The sensitivity of mass detection may hence be increased by the same amounts.

Figure 8:
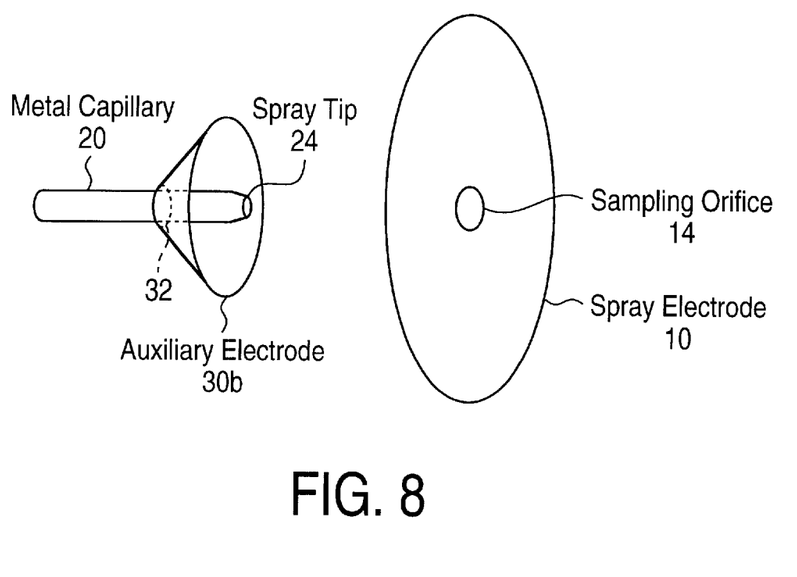
FIG. 8 is another embodiment of an ESI source of the present invention.
Figure 9:
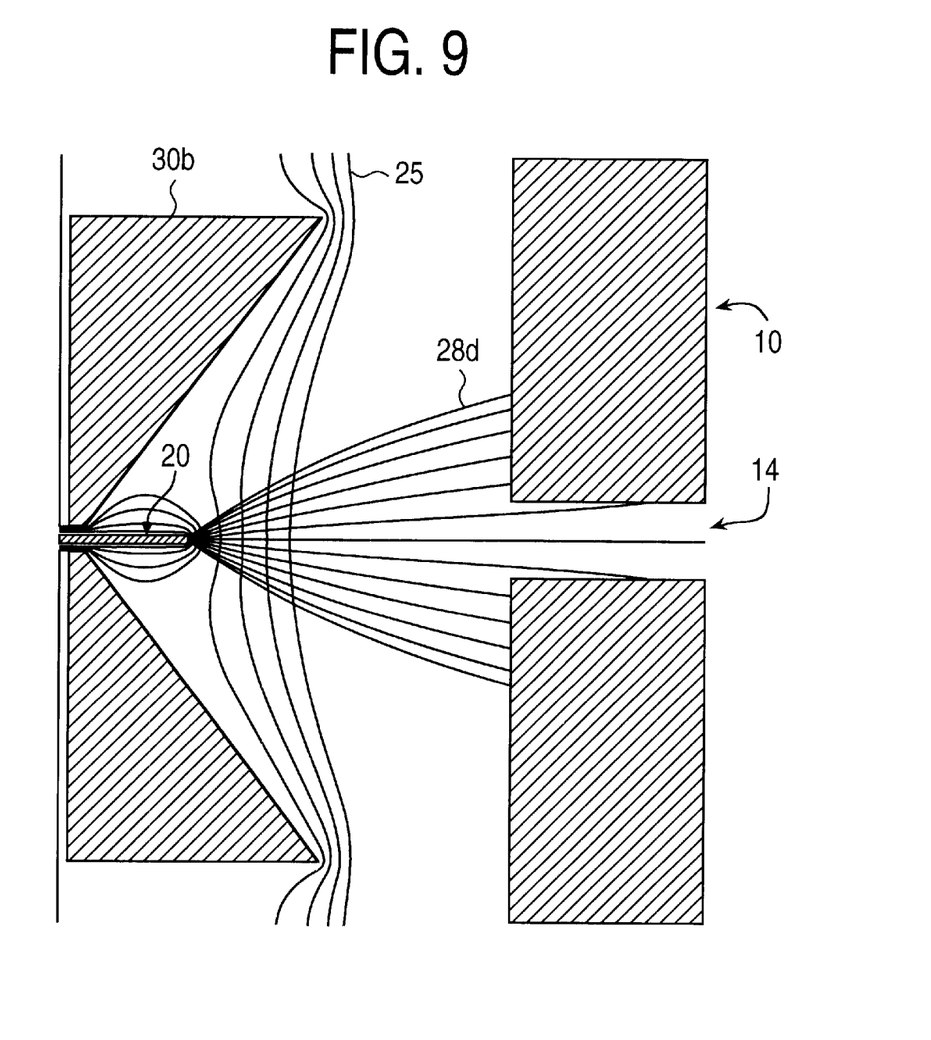
FIG. 9 is similar to FIG. 6 but using the ESI source of FIG. 8.
Figure 10:
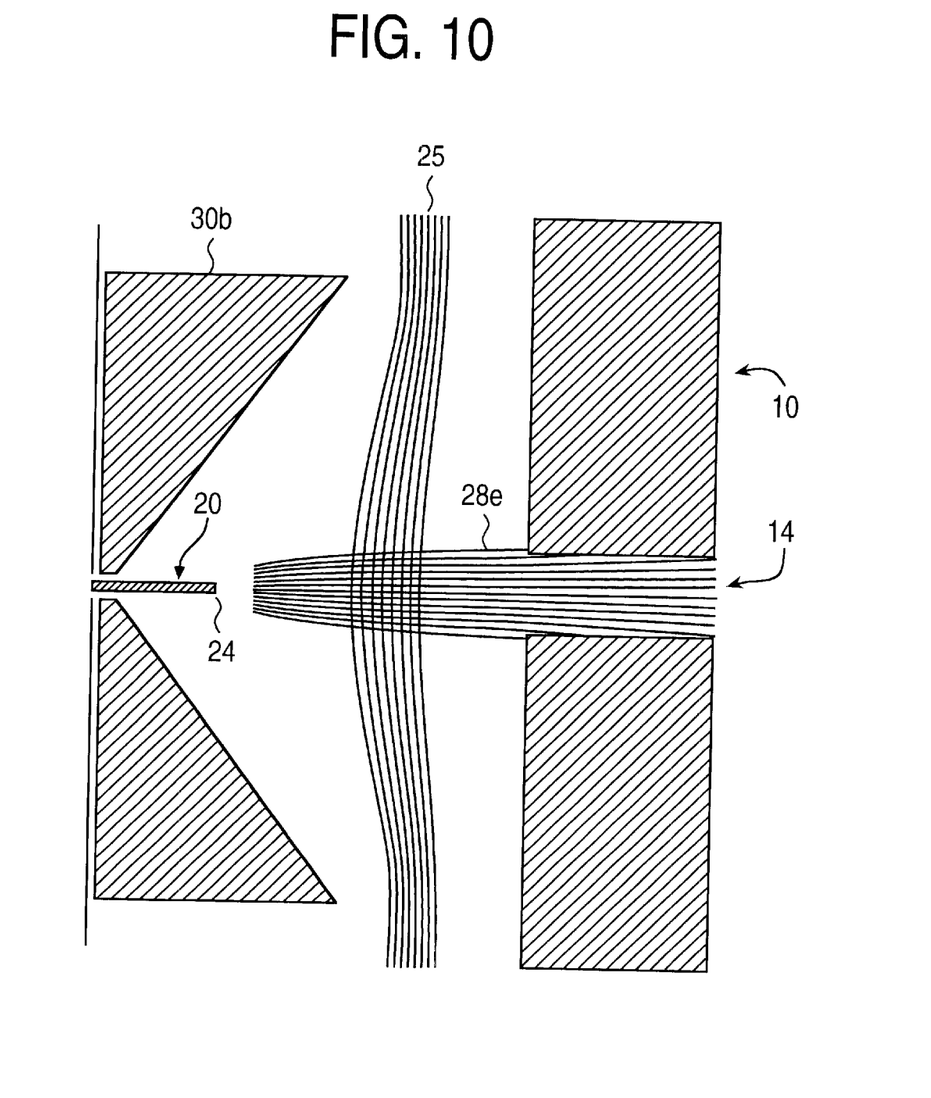
FIG. 10 is similar to FIG. 7 but using the ESI source of FIG. 8.

An alternate configuration for an auxiliary electrode 30b is illustrate in FIG. 8. In this configuration, auxiliary electrode 30b is in the form of a cone open at both ends, and positioned centrally about an optic axis of capillary 20. Cone 30b extends forwardly from a position behind tip 24 toward interface member 10. The ESI source with such a cone 30b is used in the same manner as that in FIG. 4. FIGS. 9 and 10 are the same as FIGS. 6 and 7 except with the use of auxiliary electrode 30b rather than 30a. However, due to the conical shape of auxiliary electrode 30b, an even more favorable electric field for ion focusing is obtained as best illustrated in FIG. 10, such that ion current through orifice 14 can be further increased.

Note that the auxiliary electrode in the either of the foregoing specific embodiments, is not in the ion beam path (that is, ions from tip 24 will not normally be intercepted by the auxiliary electrode). It will also be appreciated that the interface member 10 is the first electrode which is in the beam path, and specifically the interface member orifice is the first orifice encountered by the beam. The interface member orifice maintains the near atmosphere pressure differential in ESI source 6 (specifically in chamber 8 thereof) and the vacuum (typically less than $10^{-1}$ Pascal or less than $10^{-2}$ or even less than $10^{-3}$ Pascal).

In any configuration selected the alternating frequency applied to the auxiliary electrode can be determined from the pulse frequency of the pulser of the mass spectrometer (normally the two will be the same). Optimization of potentials to be applied to the auxiliary electrode can either be determined theoretically or by plotting equipotentials and ion trajectories as in FIGS. 6, 7, 9, and 10 using a computer program such as SIMION (SIMION 3D, Version 6.0 by David A. Dahl, Idaho National Engineering Laboratory, Idaho Fall, Id. 83415, (1995)). Alternatively, these can be determined experimentally by using a known analyte of constant composition introduced into capillary 22, and observing the measured signal at detector 180 while adjusting such potentials until a maximum signal is observed. Typical potential differences of the auxiliary electrode with respect to tip 24 may range from −100 to −3000 V (more typically, −500 to −3000 V, or −1000 to −3000 V) for the field enhancing potential, and from 100 to 2000 V (more typically, 400 to 1500V, or 500 to 2000 V) (foregoing for positive ions, sign may be reversed for negative ions) for the focusing enhancing potential. Of course, the frequency applied to the auxiliary electrode can also be selected by processor 220 as a function of the mass of ions to be analyzed by the mass spectrometer 120. For example, higher mass will typically have a longer flight time between tip 24 and interface member 10 such that the frequency will be lower. A preferred frequency can be calculated based on the particular ESI source configuration (electrode spacing) and potentials applied. The pulser frequency can be set in synchronization with such a preferred frequency. Alternatively, auxiliary electrode and pulser frequencies can be varied in synchronization until the strongest output signal is obtained for a given set of potentials on the electrodes. Typical frequencies will be between 500 Hz to 30 kHz (more typically 2 kHz to 20 kHz, or 5 kHz to 15 kHz).

In one experiment, an ion collector in construction of a Faraday cup was placed in the chamber 124, just behind the orifice 14 and the ion current was measured by a picoampere meter. An ESI source 6 using the planar auxiliary electrode 30a configuration as shown in FIG. 4 was used to generate ions from a sample. The following conditions were established:

Sample (Analyte): 1 mol acetic acid,
Flow rate: 2 microliter/min,
Distance between capillary tip and interface member orifice: 15 mm,
Tip potential: 2150 V (with reference to interface member of 0 V; positive ions generated)
Potential on the auxiliary electrode: (a) in the operation mode of no field switching, the potential on the auxiliary electrode is the same as that on the tip, i.e., 2150 V and (b) in the field switching mode, the potential was switched between: high, 2900V(focussing) and low, −100 V (field enhancing), and
Pulse rate: 1 kHz with 50% duty cycle.

During the entire experiment, the housing 6 was held at the atmospheric pressure while the pressure in chamber 124 was maintained at 0.8 Pascal.

Figure 11:
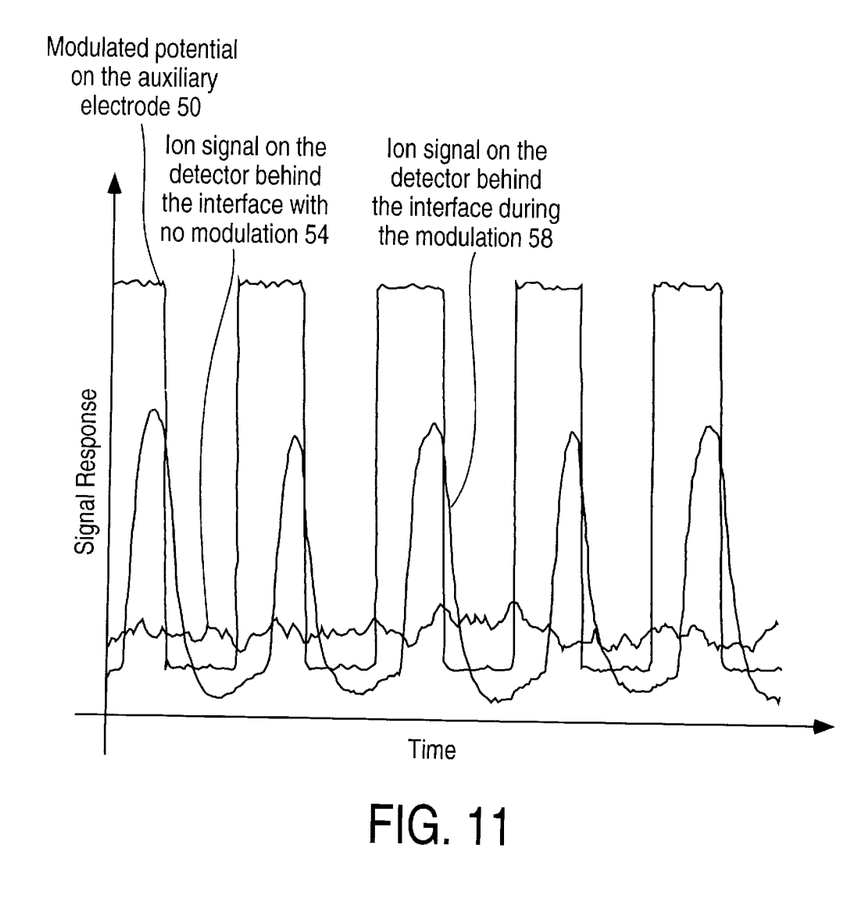
FIG. 11 is a plot illustrating the experimental result of using a method of the present invention.

The timing of the modulated potential on the auxiliary electrode is illustrated as plot 50 in FIG. 11. While the output signal at the ion collector, registered with using the modulated potential is plot 58, an output signal under the same conditions but with auxiliary electrode potential held at constant voltage of 2150 V is shown as plot 54. Note the substantial improvement in output signal (indicating higher ion current through sampling orifice 14) when the modulated electric field is provided to the auxiliary electrode. Also, it will be seen that the peaks in output signal occur just after switching the auxiliary electrode from field enhancing to focussing potential.

Various further modifications to the particular embodiments described above are, of course, possible. Accordingly, the present invention is not limited to the particular embodiments described in detail above.

What is claimed is:

1. A method of providing ions to a mass spectrometer having an interface member with an orifice through which ions are received for analysis, comprising: (a) providing a fluid at a capillary tip of an electrospray ionization source and applying a potential difference between the tip and the interface member so as to direct an ion beam from the tip toward and through the orifice; (b) applying a field enhancing potential at an auxiliary electrode so as to increase the electric field gradient from the capillary tip at least part way toward the interface member wherein the auxiliary electrode is at least partly behind the capillary tip and the field enhancing potential is lower than the tip potential when positive ions are being provided and is higher than the tip potential when negative ions are being provided.

2. A method according to claim 1 wherein the auxiliary electrode faces the interface member.

3. A method according to claim 1 wherein the field enhancing potential is applied intermittently at a predetermined frequency.

4. A method of providing ions to a mass spectrometer having an interface member with an orifice through which ions are received for analysis, comprising: (a) providing a fluid at a capillary tip of an electrospray ionization source and applying a potential difference between the tip and the interface member so as to direct an ion beam from the tip toward and through the orifice; (b) applying a focussing potential at an auxiliary electrode so as to decrease beam divergence from at least part way toward the interface member wherein the potential difference and the focussing potential are provided at a time such that the second field is provided when ions emitted from the tip during provision of the first field are intermediate the tip and interface member.

5. A method according to claim 4 wherein the auxiliary electrode faces the interface member.

6. A method according to claim 4 wherein the auxiliary electrode is at least partly behind the capillary tip, and the focussing potential is higher than the tip when positive ions are being provided and is lower than the tip when negative ions are being provided.

7. A method according to claim 6 wherein the focussing potential is applied intermittently at a predetermined frequency.

8. A method of providing ions to a mass spectrometer having an interface member with an orifice through which ions are received for analysis, comprising: (a) providing a fluid at a capillary tip of an electrospray ionization source; (b) alternately providing: a first electric field between the tip and the interface member so as to direct an ion beam from the tip toward and through the orifice; and a second electric field which decreases beam divergence from at least part way toward the interface member wherein the first and second fields are provided at a time such that the second field is provided when ions emitted from the tip during provision of the first field are intermediate the tip and interface member.

9. A method according to claim 8 wherein the mass spectrometer is a time-of-flight mass spectrometer which moves ions to be analyzed into an analyzing section of the spectrometer at a predetermined pulse rate and wherein a field enhancing potential is applied at an auxiliary electrode intermittently at a predetermined frequency so as to increase the electric field gradient from the capillary tip at least part way toward the interface member; and the frequency and pulse rate are synchronized such that a higher ion current is provided to the analyzing section than would be provided if a constant field was applied.

10. A method of providing ions to a mass spectrometer having an interface member with an orifice through which ions are received for analysis, comprising:
   (a) providing a fluid at a capillary tip of an electrospray ionization source and applying a potential difference between the tip and the interface member so as to direct an ion beam from the tip toward and through the orifice;
   (b) alternately applying to an auxiliary electrode: a field enhancing potential which increases the electric field gradient from the capillary tip at least part way toward the interface member; and a focussing potential so as to decrease beam divergence from at least part way toward the interface member wherein the field enhancing and focussing potentials are applied at a time such that the focussing potential is applied when ions emitted from the tip during application of the field enhancing potential are intermediate the tip and interface member.

11. A method according to claim 10 wherein the field enhancing potential is lower than the tip potential when positive ions are being provided and is higher than the tip potential when negative ions are being provided, and the focussing potential is higher than the tip potential when positive ions are being provided and lower than the tip potential when negative ions are being provided.

12. A method according to claim 10 wherein the mass spectrometer is a time-of-flight mass spectrometer which moves ions to be analyzed into an analyzing section of the spectrometer at a predetermined pulse rate and wherein a field enhancing potential is applied at an auxiliary electrode intermittently at a predetermined frequency so as to increase the electric field gradient from the capillary tip at least part way toward the interface member; and the frequency and pulse rate are synchronized such that a higher ion current is provided to the analyzing section than would be provided without the auxiliary electrode.

13. A method according to claim 10 wherein the auxiliary electrode faces the interface member.

14. A method according to claim 10 wherein the auxiliary electrode is at least partly behind the capillary tip.

15. A method according to claim 10 wherein the auxiliary electrode is positioned around an axis of the capillary and extends forward from a position behind the tip toward the interface member.

16. An electrospray ionization source for use with a mass spectrometer having an interface member with an orifice, comprising:
   (a) a capillary having a channel and a tip, such that when fluid is delivered to the tip through the channel and a potential applied between the tip and the interface member, an ion beam is directed from the tip toward the member,
   (b) an auxiliary electrode mounted with respect to the capillary tip, to which a field enhancing potential can be applied so as to increase the electric field gradient from the capillary tip at least part way toward the interface member wherein the auxiliary electrode is mounted at least partly behind the capillary tip.

17. An electrospray ionization source according to claim 16 wherein the auxiliary electrode is mounted such that a focussing potential can also be applied at the auxiliary electrode so as to decrease beam divergence from at least part way toward the interface member.

18. An electrospray ionization source according to claim 16 wherein the auxiliary electrode and capillary tip both face toward the interface member when the source is mounted on a mass spectrometer.

19. An electrospray ionization source according to claim 18 wherein the auxiliary electrode is positioned around an axis of the capillary and extends forward from a position behind the tip.

20. A mass spectrometer comprising:
   (a) an interface member with an orifice;
   (b) an analyzer section to receive ions which have passed through the orifice and detect them as a function of mass and charge;
   (c) an electrospray ionization source having a capillary with a channel and a tip, such that a fluid can be delivered to the tip through the channel; and
   (d) an electrode set and power supply connected to the set so as to alternately provide
      a first electric field between the tip and the interface member so as to direct an ion beam from the tip toward and through the orifice; and
      a second electric field which decreases beam divergence from at least part way toward the interface member wherein the power supply provides the first and second fields at a time such that the second field is provided when ions emitted from the tip during provision of the first field are intermediate the tip and interface member.

21. A mass spectrometer according to claim 20 wherein the mass spectrometer is a time-of-flight mass spectrometer which moves ions to be analyzed into an analyzing section of the spectrometer at a predetermined pulse rate and wherein a field enhancing potential is applied at an auxiliary electrode intermittently at a predetermined frequency so as to increase the electric field gradient from the capillary tip at least part way toward the interface member; and the frequency and pulse rate are synchronized such that a higher ion current is provided to the analyzing section than would be provided if the first field was continuously applied.

22. A mass spectrometer comprising:
   (a) an interface member with an orifice;
   (b) an analyzer section to receive ions which have passed through the orifice and detect them as a function of mass and charge; and
   (c) an electrospray ionization source having:
      (i) a capillary having a channel and a tip, such that when fluid is delivered to the tip through the channel and a potential applied between the tip and the interface member, an ion beam is directed from the tip toward the orifice; and
      (ii) an auxiliary electrode mounted with respect to the capillary tip, to which a focussing potential can be applied so as to decrease beam divergence from at least part way toward the interface member wherein said auxiliary electrode has a conical shape.

23. A mass spectrometer according to claim 22 wherein the auxiliary electrode is mounted such that a field enhancing potential can be applied thereto so as to increase the electric field gradient from the capillary tip at least part way toward the interface member.

24. A mass spectrometer according to claim 22 additionally comprising a power supply which alternately supplies the field enhancing and focussing potentials to the auxiliary electrode.

25. A mass spectrometer according to claim 24 wherein the power supply applies the field enhancing and focussing potentials at a time such that the focussing potential is applied when ions emitted from the tip during application of the field enhancing potential are intermediate the tip and interface member.

26. A mass spectrometer according to claim 25 wherein a field enhancing potential is applied at an auxiliary electrode intermittently at a predetermined frequency so as to increase the electric field gradient from the capillary tip at least part way toward the interface member, said mass spectrometer additionally comprising a processor which selects the frequency as a function of mass of the ions to be analyzed by the mass spectrometer.

27. A mass spectrometer according to claim 25 wherein the mass spectrometer is a time of flight mass spectrometer and includes a pulser which moves ions to be analyzed into an analyzing section at a predetermined pulse rate and wherein a field enhancing potential is applied at an auxiliary electrode intermittently at a predetermined frequency so as to increase the electric field gradient from the capillary tip at least part way toward the interface member; and the frequency and pulse rate are synchronized such that a higher ion current is provided to the analyzer section than would be provided without the auxiliary electrode.

28. A mass spectrometer according to claim 25 wherein the auxiliary electrode is mounted at least partly behind the capillary tip.

29. A mass spectrometer according to claim 28 wherein the auxiliary electrode and capillary tip both face toward the interface member when the source is mounted on a mass spectrometer.

30. A mass spectrometer according to claim 29 wherein the auxiliary electrode is positioned around an axis of the capillary and extends forward from a position behind the tip.

* * * * *